United States Patent [19]

Scolnick et al.

[11] Patent Number: 4,952,561

[45] Date of Patent: Aug. 28, 1990

[54] CARDIAC ATRIAL PEPTIDES

[75] Inventors: Edward M. Scolnick, Wynnewood; Robert A. Zivin, Blue Bell, both of Pa.

[73] Assignee: Merck & Co., Inc., Rahway, N.J.

[21] Appl. No.: 688,798

[22] Filed: Jan. 4, 1985

Related U.S. Application Data

[63] Continuation-in-part of Ser. No. 577,658, Feb. 7, 1984.

[51] Int. Cl.$^5$ .................. A61K 37/02; C07K 7/06; C07K 7/08; C07K 7/10
[52] U.S. Cl. ........................ 514/12; 514/13; 514/14; 514/15; 530/324; 530/325; 530/326
[58] Field of Search .................. 260/112.5 R; 514/12, 514/13, 14, 15; 530/326, 327, 328, 324, 325

[56] References Cited

U.S. PATENT DOCUMENTS

| | | | |
|---|---|---|---|
| 4,059,694 | 11/1977 | Norton et al. | 260/112.5 R |
| 4,103,004 | 7/1978 | Norton et al. | 260/112.5 R |
| 4,496,544 | 1/1985 | Needleman | 260/112.5 R |
| 4,508,712 | 4/1985 | Needleman | 514/11 |

Primary Examiner—Lester L. Lee
Attorney, Agent, or Firm—Charles M. Caruso; Donald J. Perrella; Hesna J. Pfeiffer

[57] ABSTRACT

A DNA fragment encoding at least part of the ANF protein has been molecularly cloned and its nucleotide sequence partially determined. The composition and sequence of a peptide containing 116 amino acids within the ANF gene have been determined. Biologically active subunit peptides have been identified.

6 Claims, No Drawings

CARDIAC ATRIAL PEPTIDES

This application is a continuation-in-part of our copending U.S. patent application Ser. No. 577,658 filed Feb. 7, 1984.

BACKGROUND OF THE INVENTION

It has been postulated for many years that the cardiac atria serve as sensors that are important in detecting changes in extracellular fluid volume (Gauer et al., Physiol, Rev. 43: 423, 1963). Such a receptor function for the cardiac atria is known in the case of vasopressin, the hypothalmic hormone important in regulating the osmotic concentration of the body fluids.

The postulated existence of a substance which would enhance urinary sodium excretion, and hence be involved in regulation of extracellular fluid volume, was demonstrated recently. de Bold et al., Life Sci. 28: 89, 1981, injected a partially purified extract of cardiac atria of rats into other anesthetized rats and observed a large increase in urine flow and in urinary sodium excretion. This relatively crude extract possessed the appropriate characteristics of an endogenous natriuretic substance.

In addition to its potent diuretic and natriuretic effects, properties that make the material especially appropriate to exert a major effect on body fluid volume regulation, it was also discovered that these extracts of cardiac atria have potent smooth muscle relaxant activity (Currie et al., Science 221: 71, 1983). Such action implies a potential direct role in regulating blood pressure as well as a role in regulating extracellular fluid volume.

Because of the immediately recognized importance of this discovery for understanding the regulation of body fluid volume and blood pressure and the obvious therapeutic potential of such a natural substance in the treatment of congestive heart failure and hypertension, numerous laboratories set about to isolate, characterize and chemically identify the active substance(s) in the cardiac atrial extracts. The active substance(s) in cardiac atria was called atrial natriuretic factor or ANF but has been referred to also as cardionatrin (de Bold et al., Life Sci. 33: 297-1983) and atriopeptin (Currie et al., Science 111: 67, 1984).

Peptide chemists quickly produced completely synthetic material that mimicked the biological activity of the family of peptides that have been isolated from the cardiac atria. During the initial efforts to synthesize these peptides, it became evident that production of large quantities of compounds by classical chemical techniques, whether by solid phase, solution chemistry or a combination of these procedures, would require a long time as well as being costly to produce.

An alternative to classical chemical synthesis for production of these peptides is to clone the gene for ANF using techniques known to molecular biologists. Once the genetic material that codes for ANF is available, it might be possible to incorporate this material into a suitable vector that would synthesize the ANF peptide biologically in a suitable host. If the gene could be expressed in this manner, it might be possible to produce sufficient ANF for biological testing and therapeutic use.

Because the genetically produced material will represent the peptide sequence as it is synthesized biologically within the cardiocyte, this material will provide a unique precursor that can be further processed either biologically or chemically to the final mediators of the biological responses. Also, the genetic product will provide a unique tool to develop antibodies to ANF that can be used to identify the circulating form of ANF. This is of importance since ANF might circulate as a precursor that is metabolized to its active form at its site of action. Such information is critical to determining a dosage form to be used therapeutically to enhance its duration of action in the organism and perhaps to localize its action. The latter consideration results from the possibility that enzymes localized in specific tissues could result in local production of active ANF from a precursor molecule in amounts adequate for biological action.

The therapeutic utility of ANF is in congestive heart failure where standard therapy utilizes potent diuretics in combination with peripheral vasodilating drugs. Atrial natriuretic factor combines both of these actions in one molecule which is produced naturally within the body. It is possible that the salt and water retention associated with congestive heart failure is a result of inadequate production of ANF. If such is true, genetically engineered ANF would allow for replacement of adequate quantities of the material.

In addition to its utility to treat congestive heart failure, a second major disease process which might be improved by ANF is essential hypertension. Standard therapy for hypertension utilizes diuretic and peripheral vasodilating drugs. Atrial natriuretic factor incorporates both of these characteristics. A specific use also may be found in the acute treatment of hypertensive crisis such as malignant hypertension where the powerful vasodilating effect of ANF would be paramount.

In addition to these two very broad categories of therapeutic utility, it is possible that those diseases which are characterized by decreases in renal function may benefit because of the favorable action of ANF on renal hemodynamics, especially enhancement of medullary blood flow.

OBJECTS OF THE INVENTION

It is an object of the present invention to provide a method for cloning the ANF gene. Another object is to determine the nucleotide and amino acid sequences of ANF and at least part of its precursor or precursors. A further object is to provide biologically active peptide fragments of ANF. Yet another object is to provide a method for producing ANF or parts thereof by expression of cloned DNA in an appropriate host. Still another object is to provide a vector containing the ANF gene or part thereof. Another object is to provide transformed hosts containing a vector containing the ANF gene or part thereof and being capable of expressing the peptide coded for by said gene or part thereof. These and other objects of the present invention will be apparent from the following description.

SUMMARY OF THE INVENTION

A DNA fragment encoding at least part of the rat ANF protein has been molecularly cloned and its nucleotide sequence partially determined. The composition and sequence of a peptide containing 116 amino acids within the ANF gene have been determined. Biologically active subunit peptides have been identified.

DETAILED DESCRIPTION

Polyadenylated RNA (Poly $A^{30}$ RNA) was isolated from rat cardiac atria. Oligonucleotide primers were synthesized which were complementary to the nucleotides which encode a known amino acid sequence of the ANF gene. These primers were hybridized to the poly A+ rat atrial RNA and a complementary cDNA was synthesized. This single stranded DNA was used as a template for synthesis of its complementary strand to produce a double stranded DNA corresponding to at least a portion of the ANF gene.

The double stranded DNA was modified to provide "sticky ends" and was placed into an appropriate vector. Suitable hosts, e.g. prokaryotic or eukaryotic organisms, were exposed to the resulting vector and those which stably incorporated the vector were identified and isolated.

Vector DNA was extracted from these hosts and this material was characterized. A fragment of cloned ANF DNA was selected which contained approximately 600 nucleotide base pairs. The sequence of 461 nucleotides of this fragment was determined and the corresponding amino acid sequence encoded thereby was inferred.

Knowledge of the amino acid sequence of this peptide makes possible its synthesis as well as subunits and homologues and analogues thereof thus allowing determination of the relationship between structure and function.

The ANF peptides of the present invention may be prepared from their constituent amino acids by standard methods of protein synthesis, e.g., Schroeder et al., "The Peptides", Vol. I, Academic Press, 1965, or Bodanszky et al., "Peptide Synthesis", Interscience Publishers 1966, or McOmie (ed.), "Protective Groups in Organic Chemistry", Plenum Press 1973, the disclosures of which are hereby incorporated by reference.

The peptides of the present invention also may be prepared by recombinant DNA techniques by, for example, the isolation or preparation of appropriate DNA sequences and incorporation of these sequences into vectors followed by insertion of the vectors in a suitable host and expression of the desired peptide therefrom. The use of recombinant DNA techniques is described in many published articles, for example, Maniatis et al., Molecular Cloning, A Laboratory Manual, Cold Spring Harbor, New York 1982, the disclosure of which is hereby incorporated by reference. Modification of the nucleotides coding for the peptides of the present invention according to known techniques permits the preparation via recombinant DNA techniques of peptides having altered amino acid sequences of the peptides of the present invention. Certain of these amino acids may be coded for by more than one triplet nucleotide sequence. It is to be understood that the disclosed nucleotide sequence is to include other codons coding for the same amino acid, e.g., the codons CGA and AGA each code for arginine.

Suitable hosts for expression of the ANF peptides include prokaryotic organisms such as *E. coli* and *B. subtilis*, and eukaryotic organsims such as *Saccharomyces cerevisiae* and Chinese hamster ovary cells. It is also to be understood that these proteins can be expressed directly in a mammalian species by means of appropriate expression vectors such as vaccinia, varicella zoster, adeno or herpes simplex viruses.

The peptides of the present invention are useful individually or in combination to treat disorders of electrolyte balance and/or altered vascular resistance in a mammalian species in amount of from about 10 to about 2000 picomoles/kg/min., preferably from about 100 to about 1000 picomoles/kg/min. The peptides may be administered by intravenous infusion, for example in a suitable physiologically acceptable carrier, e.g., saline or phosphate buffered saline.

The subunit peptides of ANF or the amide thereof which are included within the ambit of the present invention More specifically, the peptide subunits of include peptides having the amino acid sequences:

X Cys Phe Gly Gly Arg A Asp Arg Ile Gly Ala Gln Ser Gly Leu Gly Cys Asn Ser-Y wherein X is:

Ser—
Ser—Ser—
Arg—Ser—Ser—
Arg—Arg—Ser—Ser—
Leu—Arg—Arg—Ser—Ser—
Ser—Leu—Arg—Arg—Ser—Ser—
Arg—Ser—Leu—Arg—Arg—Ser—Ser—
Pro—Arg—Ser—Leu—Arg—Arg—Ser—Ser—
Gly—Pro—Arg—Ser—Leu—Arg—Arg—Ser—Ser—
Ala—Gly—Pro—Arg—Ser—Leu—Arg—Art—Ser—Ser—
or
Leu—Ala—Gly—Pro—Arg—Ser—Leu—Arg—Arg—Ser—Ser—;

A is Ile or Met and wherein Y is the carboxyl group of serine or the, or

Phe
Phe Arg
Phe Arg Tyr
Phe Arg Tyr Arg or
Phe Arg Tyr Arg Arg, provided that: when Y is Phe, Phe Arg or the Phe Arg Tyr, A is not Ile.

Specific compounds of the present invention include the following peptides wherein A is Ile or Met:

1. Cys Phe Gly Gly Arg Met Asp Arg Ile Gly Ala Glu Ser Gly Leu Gly Cys Asn Ser
2. Ser Cys Phe Gly Gly Arg Met Asp Arg Ile Gly Ala Glu Ser Gly Leu Gly Cys Asn Ser
3. Ser Ser Cys Phe Gly Gly Arg Met Asp Arg Ile Gly Ala Glu Ser Gly Leu Gly Cys Asn Ser
4. Arg Ser Ser Cys Phe Gly Gly Arg Met Asp Arg Ile Gly Ala Glu Ser Gly Leu Gly Cys Asn Ser
5. Arg Arg Ser Ser Cys Phe Gly Gly Arg Met Asp Arg Ile Gly Ala Glu Ser Gly Leu Gly Cys Asn Ser
6. Leu Arg Arg Ser Ser Cys Phe Gly Gly Arg Met Asp Arg Ile Gly Ala Glu Ser Gly Leu Gly Cys Asn Ser
7. Ser Leu Arg Arg Ser Ser Cys Phe Gly Gly Arg Met Asp Arg Ile Gly Ala Glu Ser Gly Leu Gly Cys Asn Ser
8. Arg Ser Leu Arg Arg Ser Ser Cys Phe Gly Gly Arg Met Asp Arg Ile Gly Ala Glu Ser Gly Leu Gly Cys Asn Ser
9. Pro Arg Ser Leu Arg Arg Ser Ser Cys Phe Gly Gly Arg Met Asp Arg Ile Gly Ala Glu Ser Gly Leu Gly Cys Asn Ser
10. Gly Pro Arg Ser Leu Arg Arg Ser Ser Cys Phe Gly Gly Arg Met Asp Arg Ile Gly Ala Glu Ser Gly Leu Gly Cys Asn Ser
11. Ala Gly Pro Arg Ser Leu Arg Arg Ser Ser Cys Phe Gly Gly Arg Met Asp Arg Ile Gly Ala Glu Ser Gly Leu Gly Cys Asn Ser
12. Leu Ala Gly Pro Arg Ser Leu Arg Arg Ser Ser Cys Phe Gly Gly Arg Met Asp Arg Ile Gly Ala Glu Ser Gly Leu Gly Cys Asn Ser
13. Cys Phe Gly Gly Arg Met Asp Arg Ile Gly Ala Glu Ser Gly Leu Gly Cys Asn Ser Phe
14. Ser Cys Phe Gly Gly Arg Met Asp Arg Ile Gly Ala Glu Ser Gly Leu Gly Cys Asn Ser Phe
15. Ser Ser Cys Phe Gly Gly Arg Met Asp Arg Ile Gly Ala Glu Ser Gly Leu Gly Cys Asn Ser Phe

16. Arg Ser Ser Cys Phe Gly Gly Arg Met Asp Arg Ile Gly Ala Glu Ser Gly Leu Gly Cys Asn Ser Phe
17. Arg Arg Ser Ser Cys Phe Gly Gly Arg Met Asp Arg Ile Gly Ala Glu Ser Gly Leu Gly Cys Asn Ser Phe
18. Leu Arg Arg Ser Ser Cys Phe Gly Gly Arg Met Asp Arg Ile Gly Ala Glu Ser Gly Leu Gly Cys Asn Ser Phe
19. Ser Leu Arg Arg Ser Ser Cys Phe Gly Gly Arg Met Asp Arg Ile Gly Ala Glu Ser Gly Leu Gly Cys Asn Ser Phe
20. Arg Ser Leu Arg Arg Ser Ser Cys Phe Gly Gly Arg Met Asp Arg Ile Gly Ala Glu Ser Gly Leu Gly Cys Asn Ser Phe
21. Pro Arg Ser Leu Arg Arg Ser Ser Cys Phe Gly Gly Arg Met Asp Arg Ile Gly Ala Glu Ser Gly Leu Gly Cys Asn Ser Phe
22. Gly Pro Arg Ser Leu Arg Arg Ser Ser Cys Phe Gly Gly Arg Met Asp Arg Ile Gly Ala Glu Ser Gly Leu Gly Cys Asn Ser Phe
23. Ala Gly Pro Arg Ser Leu Arg Arg Ser Ser Cys Phe Gly Gly Arg Met Asp Arg Ile Gly Ala Glu Ser Gly Leu Gly Cys Asn Ser Phe
24. Leu Ala Gly Pro Arg Ser Leu Arg Arg Ser Ser Cys Phe Gly Gly Arg Met Asp Arg Ile Gly Ala Glu Ser Gly Leu Gly Cys Asn Ser Phe
25. Cys Phe Gly Gly Arg Met Asp Arg Ile Gly Ala Glu Ser Gly Leu Gly Cys Asn Ser Phe Arg
26. Ser Cys Phe Gly Gly Arg Met Asp Arg Ile Gly Ala Glu Ser Gly Leu Gly Cys Asn Ser Phe Arg
27. Ser Ser Cys Phe Gly Gly Arg Met Asp Arg Ile Gly Ala Glu Ser Gly Leu Gly Cys Asn Ser Phe Arg
28. Arg Ser Ser Cys Phe Gly Gly Arg Met Asp Arg Ile Gly Ala Glu Ser Gly Leu Gly Cys Asn Ser Phe Arg
29. Arg Arg Ser Ser Cys Phe Gly Gly Arg Met Asp Arg Ile Gly Ala Glu Ser Gly Leu Gly Cys Asn Ser Phe Arg
30. Leu Arg Arg Ser Ser Cys Phe Gly Gly Arg Met Asp Arg Ile Gly Ala Glu Ser Gly Leu Gly Cys Asn Ser Phe Arg
31. Ser Leu Arg Arg Ser Ser Cys Phe Gly Gly Arg Met Asp Arg Ile Gly Ala Glu Ser Gly Leu Gly Cys Asn Ser Phe Arg
32. Arg Ser Leu Arg Arg Ser Ser Cys Phe Gly Gly Arg Met Asp Arg Ile Gly Ala Glu Ser Gly Leu Gly Cys Asn Ser Phe Arg
33. Pro Arg Ser Leu Arg Arg Ser Ser Cys Phe Gly Gly Arg Met Asp Arg Ile Gly Ala Glu Ser Gly Leu Gly Cys Asn Ser Phe Arg
34. Gly Pro Arg Ser Leu Arg Arg Ser Ser Cys Phe Gly Gly Arg Met Asp Arg Ile Gly Ala Glu Ser Gly Leu Gly Cys Asn Ser Phe Arg
35. Ala Gly Pro Arg Ser Leu Arg Arg Ser Ser Cys Phe Gly Gly Arg Met Asp Arg Ile Gly Ala Glu Ser Gly Leu Gly Cys Asn Ser Phe Arg
36. Leu Ala Gly Pro Arg Ser Leu Arg Arg Ser Ser Cys Phe Gly Gly Arg Met Asp Arg Ile Gly Ala Glu Ser Gly Leu Gly Cys Asn Ser Phe Arg
37. Cys Phe Gly Gly Arg Met Asp Arg Ile Gly Ala Glu Ser Gly Leu Gly Cys Asn Ser Phe Arg Tyr
38. Ser Cys Phe Gly Gly Arg Met Asp Arg Ile Gly Ala Glu Ser Gly Leu Gly Cys Asn Ser Phe Arg Tyr
39. Ser Ser Cys Phe Gly Gly Arg Met Asp Arg Ile Gly Ala Glu Ser Gly Leu Gly Cys Asn Ser Phe Arg Tyr
40. Arg Ser Ser Cys Phe Gly Gly Arg Met Asp Arg Ile Gly Ala Glu Ser Gly Leu Gly Cys Asn Ser Phe Arg Tyr
41. Arg Arg Ser Ser Cys Phe Gly Gly Arg Met Asp Arg Ile Gly Ala Glu Ser Gly Leu Gly Cys Asn Ser Phe Arg Tyr
42. Leu Arg Arg Ser Ser Cys Phe Gly Gly Arg Met Asp Arg Ile Gly Ala Glu Ser Gly Leu Gly Cys Asn Ser Phe Arg Tyr
43. Arg Ser Leu Arg Arg Ser Ser Cys Phe Gly Gly Arg Met Asp Arg Ile Gly Ala Glu Ser Gly Leu Gly Cys Asn Ser Phe Arg Tyr
44. Pro Arg Ser Leu Arg Arg Ser Ser Cys Phe Gly Gly Arg Met Asp Arg Ile Gly Ala Glu Ser Gly Leu Gly Cys Asn Ser Phe Arg Tyr
45. Gly Pro Arg Ser Leu Arg Arg Ser Ser Cys Phe Gly Gly Arg Met Asp Arg Ile Gly Ala Glu Ser Gly Leu Gly Cys Asn Ser Phe Arg Tyr
46. Ala Gly Pro Arg Ser Leu Arg Arg Ser Ser Cys Phe Gly Gly Arg Met Asp Arg Ile Gly Ala Glu Ser Gly Leu Gly Cys Asn Ser Phe Arg Tyr
47. Leu La Gly Pro Arg Ser Leu Arg Arg Ser Ser Cys Phe Gly Gly Arg Met Asp Arg Ile Gly Ala Glu Ser Gly Leu Gly Cys Asn Ser Phe Arg Tyr
48. Cys Phe Gly Gly Arg A Asp Arg Ile Gly Ala Glu Ser Gly Leu Gly Cys Asn Ser Phe Arg Tyr Arg
49. Ser Cys Phe Gly Gly Arg A Asp Arg Ile Gly Ala Glu Ser Gly Leu Gly Cys Asn Ser Phe Arg Tyr Arg
50. Ser Ser Cys Phe Gly Gly Arg A Asp Arg Ile Gly Ala Glu Ser Gly Leu Gly Cys Asn Ser Phe Arg Tyr Arg
51. Arg Ser Ser Cys Phe Gly Gly Arg A Asp Arg Ile Gly Ala Glu Ser Gly Leu Gly Cys Asn Ser Phe Arg Tyr Arg
52. Arg Arg Ser Ser Cys Phe Gly Gly Arg A Asp Arg Ile Gly Ala Glu Ser Gly Leu Gly Cys Asn Ser Phe Arg Tyr Arg
53. Leu Arg Arg Ser Ser Cys Phe Gly Gly Arg A Asp Arg Ile Gly Ala Glu Ser Gly Leu Gly Cys Asn Ser Phe Arg Tyr Arg
54. Ser Leu Arg Arg Ser Ser Cys Phe Gly Gly Arg A Asp Arg Ile Gly Ala Glu Ser Gly Leu Gly Cys Asn Ser Phe Arg Tyr Arg
55. Arg Ser Leu Arg Arg Ser Ser Cys Phe Gly Gly Arg A Asp Arg Ile Gly Ala Glu Ser Gly Leu Gly Cys Asn Ser Phe Arg Tyr Arg
56. Pro Arg Ser Leu Arg Arg Ser Ser Cys Phe Gly Gly Arg Met A Asp Arg Ile Gly Ala Glu Ser Gly Leu Gly Cys Asn Ser Phe Arg Tyr Arg
57. Gly Pro Arg Ser Leu Arg Arg Ser Ser Cys Phe Gly Gly Arg Met A Asp Arg Ile Gly Ala Glu Ser Gly Leu Gly Cys Asn Ser Phe Arg Tyr Arg
58. Ala Gly Pro Arg Ser Leu Arg Arg Ser Ser Cys Phe Gly Gly Arg Met A Asp Arg Ile Gly Ala Glu Ser Gly Leu Gly Cys Asn Ser Phe Arg Tyr Arg
59. Leu Ala Gly Pro Arg Ser Leu Arg Arg Ser Ser Cys Phe Gly Gly Arg Met A Asp Arg Ile Gly Ala Glu Ser Gly Leu Gly Cys Asn Ser Phe Arg Tyr Arg
60. Cys Phe Gly Gly Arg Met A Asp Arg Ile Gly Ala Glu Ser Gly Leu Gly Cys Asn Ser Phe Arg Tyr Arg Arg
61. Ser Cys Phe Gly Gly Arg Met A Asp Arg Ile Gly Ala Glu Ser Gly Leu Gly Cys Asn Ser Phe Arg Tyr Arg Arg
62. Ser Ser Sys Phe Gly Gly Arg A Asp Arg Ile Gly Ala Glu Ser Gly Leu Gly Cys Asn Ser Phe Arg Tyr Arg Arg
63. Arg Ser Ser Cys Phe Gly Gly Arg Met A Asp Arg Ile Gly Ala Glu Ser Gly Leu Gly Cys Asn Ser Phe Arg Tyr Arg Arg

64. Arg Arg Ser Ser Cys Phe Gly Gly Arg Met A Asp Arg Ile Gly Ala Glu Ser Gly Leu Gly Cys Asn Ser Phe Arg Tyr Arg Arg
65. Leu Arg Arg Ser Ser Cys Phe Gly Gly Arg A Asp Arg Ile Gly Ala Glu Ser Gly Leu Gly Cys Asn Ser Phe Arg Tyr Arg Arg
66. Ser Leu Arg Arg Ser Ser Cys Phe Gly Gly Arg A Asp Arg Ile Gly Ala Glu Ser Gly Leu Gly Cys Asn Ser Phe Arg Tyr Arg Arg
67. Arg Ser Leu Arg Arg Ser Ser Cys Phe Gly Gly Arg A Asp Arg Ile Gly Ala Glu Ser Gly Leu Gly Cys Asn Ser Phe Arg Tyr Arg Arg
68. Pro Arg Ser Leu Arg Arg Ser Ser Cys Phe Gly Gly Arg A Asp Arg Ile Gly Ala Glu Ser Gly Leu Gly Cys Asn Ser Phe Arg Tyr Arg Arg
69. Gly Pro Arg Ser Leu Arg Arg Ser Ser Cys Phe Gly Gly Arg A Asp Arg Ile Gly Ala Glu Ser Gly Leu Gly Cys Asn Ser Phe Arg Tyr Arg Arg
70. Ala Gly Pro Arg Ser Leu Arg Arg Ser Ser Cys Phe Gly Gly Arg A Asp Arg Ile Gly Ala Glu Ser Gly Leu Gly Cys Asn Ser Phe Arg Tyr Arg Arg
71. Leu Ala Gly Pro Arg Ser Leu Arg Arg Ser Ser Cys Phe Gly Gly Arg A Asp Arg Ile Gly Ala Glu Ser Gly Leu Gly Cys Asn Ser Phe Arg Tyr Arg Arg

It is to be understood that the peptides of the present invention comprise both linear peptides as well as cyclic peptides formed by intramolecular bonds, in particular, by disulfide bonds between cysteine residues.

The following examples illustrate the present invention without, however, limiting the same thereto. The disclosure of each reference mentioned in the following examples is hereby incorporated by reference.

EXAMPLE 1

RNA Isolation 300 female Sprague Dawley rats were anesthetized by nitrogen intoxication and each was quickly dissected to remove both cardiac atria. The atria were immediately frozen in liquid nitrogen. The total yield was 16 grams of tissue. The atria were processed for RNA isolation by the guanidine thiocyanate-CsCl method of Raymondjean et al., Biochemie 65:65–70, 1983. The RNA was stored at −20° C. under ethanol until used.

EXAMPLE 2

Poly A+ RNA isolation

The isolated total RNA was fractionated over oligo dT cellulose (Type 7, PL Biochemicals) to yield polyadenylated RNA (poly A+ RNA) by the method of Aviv et al., Proc. Nat. Acad Sci. 69:1408–1412, 1972, with the following modifications: 75 mg of oligo dT cellulose was used; loading wash buffer was 0.2M NaCl, 10 mM Hepes KOH, 6.9, 0.05% SDS; elution buffer was 10 mM Hepes KOH pH 6.9, 0.5% SDS. The yield was 12 μg Poly A+ RNA/gram atria (192 μg).

EXAMPLE 3

Synthesis of Oligonucleotide Primers

All primers used in this work were synthesized on a Bachem manual synthesizer (Bachem Fine Chemicals, Torrance, CA) employing the triester chemistry method (Tan. et al., Cold Spring Harbor Symposium on Quantitative Biology 47, part 1: 383–391 1982). All monomer-resin and protected dimer oligonucleotide reagents were also obtained from Bachem. Operation was as described by the manufacturer. The 16 member pool of ANF 11 base oligonucleotides was synthesized in one run, starting with 24 mg of adenosine dimethoxytrityl (DMT) bound to 1% crosslinked polystyrene support resin. The five subsequent cycles of dimer addition, utilizing 40 mg dimer/cycle for single additions, and 40 mg each desired dimer for heterogenicity at indicated sites, resulted in the production of the following pool of 16 oligonucleotides:

```
3' A C A A A A C C A C C 5'    3' A C A A A G C C A C C 5'
   A C A A A A C C C C C          A C A A A G C C C C C
   A C A A A A C C G C C          A C A A A G C C G C C
   A C A A A A C C T C C          A C A A A G C C T C C
   A C G A A A C C A C C          A C G A A G C C A C C
   A C G A A A C C C C C          A C G A A G C C C C C
   A C G A A A C C G C C          A C G A A G C C G C C
   A C G A A A C C T C C          A C G A A G C C T C C
```

The oligonucleotides were deprotected and purified on cross-linked dextran (G25 Sephadex) as described by the manufacturer.

The creatine kinase primer, a single 11 base sequence of 3' T T C T G G C T G G A 5', was synthesized as above.

EXAMPLE 4 cDNA Synthesis

First and second strand cDNA syntheses were carried out by the "one pot" sequential method (Wickens et al., J. Biol. Chem. 253: 2483–2495, 1977) with the following modifications: in the first strand reaction, in a total volume of 250 μl were 46 μg poly A+ atrial RNA; 175 units human placental ribonuclease inhibitor: 3 μg of the creatine kinase 11 base primer; 3 μg of the ANF 11 base, 16 member pool of primers; and 208 units AMV (avian myeloblastosis virus) reverse transcriptase (Seikagaku America, Lot No. 83A011). No oligo dT primer was added. In the second strand reaction, in a volume of 460 μl, were 34 microcuries of $\alpha$-$^{32}$P-deoxycytidine triphosphate (400 curies/millimole); and 100 units DNA polymerase 1, Klenow fragment (Boehringer Mannheim, Indianapolis, IN, Lot No. 1333425). Incubation was for 2.5 hours at 15° C. The cDNA mix was phenol extracted, and ethanol precipitated according to Maniatis et al., Molecular Cloning, A Laboratory Manual, Cold Spring Harbor Laboratory Press, Cold Spring Harbor, NY, 1982, pages 458,.461. The precipitated cDNA was dried under vacuum.

EXAMPLE 5

Conversion of cDNA "Hairpin Structure" to Linear Form by Mung Bean Nuclease

In order to insert cDNA into plasmid vectors for cloning, it is necessary to cleave the "hairpin structure" formed during synthesis into a linear form possessing accessible termini at each end of the molecule (Efstratiadis et al., Cell 7:279, 1976). This was carried out as follows: The cDNA previously synthesized in Example 4 was resuspended in 170 μl H$_2$O, to which was added 50 μl 25% glycerol; 25 μl buffer (300 mM NaOAc, pH 4.7, 500 mM NaCl, 10 mM ZnCl$_2$); and 125 units Mung bean nuclease in 5μl (PL Biochemicals, Lot No. 912-7). After incubation at 38° C. for 30 minutes, the reaction was terminated by the addition of 25 μl of 0.8M Tris HCl pH 8.5, and 50 mM Na$_2$ EDTA. The digested material was phenol extracted (twice) and ethanol precipitated as described by Maniatis et al, op. cit.

EXAMPLE 6

Addition of oligo dC to 3' ends of cDNA

To allow insertion of cDNA into oligo deoxyguanosine (dG) "tailed" pBR322 (New England Nuclear, Boston, MA), oligo deoxycytidine (dC) "tails" were added following the procedure of Maniatis et al., op. cit., page 241, except that in the reaction mix of 100 μl was the previously synthesized and Mung bean nuclease treated cDNA, 100 uCi of [α-$^{32}$P]-dCTP (400 ci/mM) and 75 units terminal deoxynucleotide transferase, (PL Biochemicals, Lot No. 730-17).

The reaction was carried out at 37° C. for 90 seconds, then stopped by the addition of EDTA to 5 mM. The reaction mix was phenol extracted, and ethanol precipitated twice (Maniatis et al., op. cit., pages 458, 461). After drying under vacuum, the mixture was resuspended in 50 μl H$_2$O and stored at −20° C. until further use.

EXAMPLE 7

Vector/cDNA Annealing and Cell Transformation 50 ng of pBR322 oligo dG cloning vector (New England Nuclear, Lot No. 1734-266) was annealed with 1 μl of a 1/10 dilution of the cDNA in a volume of 50 μl (Maniatis et al., op. cit., p. 240). After annealing, the reaction mix was stored at −20° C. until use.

5 μl of the above mix was used to transform *E. coli* strain MM294 in 210 μl of standard transformation buffer (TFB) (Hanahan, 1983, J. Mol. Biol. 166: 557-580). Each of twenty 100 mm Petri dishes containing 30 ml LM agar (lacking magnesium) with 17 μl tetracycline per ml was inoculated with 100 μl of SOC media (Hanahan, op. cit.) containing the transformed *E. coli.* Each dish yielded approximately 200 colonies after 14 hours of incubation at 37° C.

EXAMPLE 8

Preparation of Filters for Oligonucleotide Probe Screening

Two sets of filter lifts of the colonies from Example 7 were prepared off each Petri dish, using 82 mm nitrocellulose disks (type HAHY, Millipore Corp.) (Maniatis et al., op. cit., p. 318). After several hours growth at 30° C. (second lift grown at of filters were incubated overnight at 37° C. on Luria Broth (LB) plates (Maniatis et al., op. cit., p. 440) containing 10 μg/ml chloramphenicol. The filters were then processed for DNA hybridization (Maniatis et al., op. cit., p. 314). The original dishes from which colonies were lifted were wrapped in parafilm and stored at 4° C.

EXAMPLE 9

γ-$^{32}$P Labeling of Oligonucleotide Probes

Two 16 member pools of 14 base long oligonucleotides were used as probes. The sequences of the probes were derived from the partial amino acid sequence of "pro-ANF" (trytophan-threonine-glycine-glutamic acid-valine). The nucleotide sequences were:

| Pool No. 1 | 3' A C C T G * C C * C T C C A 5' |
|---|---|
| Pool No. 2 | 3' A C C T G * C C * C T T C A 5' |

(* = any of A, G, C, T)

250 ng of each probe pool was labelled using bacteriophage T4 polynucleotide kinase (12 units, lot 35, New England Biolabs) and [γ-$^{32}$P]-ATP (adenosine triphosphate (0.3 mCi; 3000 Ci/mM, Amersham Corp.) in a total volume of 30 μl (Maniatis et al., op. cit., p. 122). The labeled probe was separated from unincorporated ATP by chromatography on C-18 resin, an 18 carbon straight chain alkyl substituted silanol resin having a particle size of 55-105 microns (μBondapak, Waters/Millipore Corp.) as follows: an RT-20 microliter pipette tip (Rainin Corp., Woburn, Ma) was plugged with siliconized glass wool (Maniatis et al., supra, p. 437). Atop the plug was added a few milligrams of C-18 resin. Another plug of glass wool was inserted, creating a glass wool-resin-glass wool "sandwich." Several ml of 0.1M Na acetate, pH 4.9, were forced through the "column" by gentle N$_2$ pressure (1-3 psig), followed by 3 applications each of 190 μl 25% acetonitrile (UV grade, Burdick and Jackson, Muskegon, Michigan) and of 190 μl of 0.1M Na acetate, pH 4.9. The reaction mixture, previously diluted to 0.6 ml in 0.1M Na acetate, was passed through the column twice, again under N$_2$ pressure. The column was then washed with 3 applications of 190 μl H$_2$O. Elution of the probe was achieved by passage of 2×100 μl aliquots of 25% acetonitrile. A separate column was run for each oligonucleotide pool. The labeled probes are stored in this solvent at −70° C., until use. Pool No. 1 had 125,000 cpm/μl,; Pool No. 2 had 70,000.

EXAMPLE 10

Screening of Filters with $^{32}$P labeled Oligonucleotide Probes

The 2 sets of filters (40 total) from Example 8 were washed for 2 hours in 250 ml of 1M NaCl, 50 mM Tris-HCl, pH 8, 1 mM Na$_2$EDTA, 0.1% SDS at 42° C. with agitation. They were then "prehybridized" in 100 ml of a solution containing 10X Denhart's solution (Maniatis et al., op. cit., p. 448), 100 μl/ml denatured salmon sperm DNA (Maniatis et al., supra, p. 327) 6X NET (0.9M NaCl, 90 mM Tris HCl 8.3, 6 mM Na$_2$EDTA), 0.1% SDS at 65° C. for 4 hours with agitation. The temperature was allowed to drop to 50° C. at which point the prehybridization mix was decanted and replaced with 20 ml of 6X NET, 0.1% SDS, 250 μg/ml E. coli t-RNA (Boehringer Mannheim, Indianapolis, Indiana) and 50 μl each of the two labeled oligonucleotide pools from Example 9. This mixture was kept at 37° C. for 9 hours, with constant agitation. (Suggs, et al., 1981, p. 683 in: Developmental Biology Using Purified Genes; D. Brown, editor, Academic Press, NY).

The filters were then washed 4 times for 5 minutes each in 500 ml 6X NET at 8° C. The damp filters were exposed to XAR film (Kodak, Rochester, NY) at −70° C. with a Cronex lightning plus intensifying screen (du Pont, Wilmington, DE) for 4 hours. The filters were then washed for 5 minutes in 600 ml of 6X NET at 3420 C., exposed to film overnight at −70° C., and finally washed again for 5 minutes at 39° C. in 6X NET. After this last wash, the filters were again exposed to film. Approximately 70 "blotted colonies" retained more of the hybridized labelled probe than their neighbors. The original colonies corresponding to these "hot" blotted colonies were picked with sterile toothpicks and transferred to each of two new LB plates containing 17 μg/ml tetracycline and grown overnight at 37° C. Filter lifts were prepared (as described above) and grown overnight at 37° C. on LB plates containing 25 μg/ml chloramphenicol and then processed for DNA hybridization. These filter lifts were washed and prehybridized as above (but in 50 ml), then each lift was hybridized to one of the two oligonucleotide pools (Example 9) in 15 ml hybridization buffer, using 25 μl of a single pool. After 2 hours at 37° C., the filters were washed 4 times at room temperature for 5 minutes each in 6X NET, then exposed to film (as described above). The filters were again washed, at 40° C., for 5 minutes in 6X NET and again exposed to film. Four colonies on filters hybridized to Pool No. 1 retained significantly more of the hybridized labelled probe than the other colonies.

chromatography (Bethesda Research Laboratories). The 600 bp insert was processed for base specific cleavage and the resultant mixtures were run on 6% and 20% acrylamide gels for sequence determination (Maxim et al. op. cit.). The 461 bp sequence obtained represents that portion of the 750 bp insert starting at the internal PST-1 site and moving towards the 5' end of the gene. In the sequence presented position 81 represents that nucleotide that is closest to the 5' end of the gene. This nucleotide sequence and the amino acids inferred therefrom follow:

| ATG | GAT | TTC | AAG | AAC | CTG | CTA | GAC | CAC | CTA | GAG | GAG | AAG | ATG |
|-----|-----|-----|-----|-----|-----|-----|-----|-----|-----|-----|-----|-----|-----|
| Met | Asp | Phe | Lys | Asn | Leu | Leu | Asp | His | Leu | Glu | Glu | Lys | Met |
| CCG | GTA | GAA | GAT | GAG | GTC | ATG | CCT | CCG | CAG | GCC | CTG | AGC | GAG |
| Pro | Val | Glu | Asp | Glu | Val | Met | Pro | Pro | Gln | Ala | Leu | Ser | Glu |
| CAG | ACC | GAT | GAA | GCG | GGG | GCG | GCA | CTT | AGC | TCC | CTC | TCT | GAG |
| Gln | Thr | Asp | Glu | Ala | Gly | Ala | Ala | Leu | Ser | Ser | Leu | Ser | Glu |
| GTG | CCT | CCC | TGG | ACT | GGG | GAA | GTC | AAC | CCG | TCT | CAG | AGA | GAT |
| Val | Pro | Pro | Trp | Thr | Gly | Glu | Val | Asn | Pro | Ser | Gln | Arg | Asp |
| GGA | GGT | GCT | CTC | GGG | CGC | GGC | CCC | TGG | GAC | CCC | TCC | GAT | AGA |
| Gly | Gly | Ala | Leu | Gly | Arg | Gly | Pro | Trp | Asp | Pro | Ser | Asp | Arg |
| TCT | GCC | CTC | TGA | AAA | AGC | AAA | CTG | AGG | GCT | CTG | CTC | GCT | GGC |
| Ser | Ala | Leu | Leu | Lys | Ser | Lys | Leu | Arg | Ala | Leu | Leu | Ala | Gly |
| CCT | CGG | AGC | CTG | CGA | AGG | TCA | AGC | TGC | TTC | GGG | GGT | AGG | ATT |
| Pro | Arg | Ser | Leu | Arg | Arg | Ser | Ser | Cys | Phe | Gly | Gly | Arg | Ile |
| GAC | AGG | ATT | GGA | GCC | CAG | AGC | GGA | CTA | GGC | TGC | AAC | AGC | TTC |
| Asp | Arg | Ile | Gly | Ala | Gln | Ser | Gly | Leu | Gly | Cys | Asn | Ser | Phe |
| CGG | TAC | CGA | AGA | TAA | CAG | CCA | AAT | CTG | CTC | GAG | CAG | ATC | GCA |
| Arg | Tyr | Arg | Arg | TER |     |     |     |     |     |     |     |     |     |
| AAA | GAT | CCC | AAG | CCC | TTG | CGG | TGT | GTC | ACA | CAG | CTT | GGT | CGC |
| ATT | GCC | ACT | GAG | AGG | TGG | TGA | ATA | CCC | TCC | TGG | AGC | TGC | AG  |

EXAMPLE 11

Restriction Analysis of Hybridization Positive Colonies

The four colonies (Nos. 1-4) that hybridized to Pool No. 1 were picked off the original plate and grown overnight in 5 ml LB broth containing 17 μg/ml tetracycline and then processed to extract plasmid DNA (Maniatis et al., op. cit., p. 368). Upon digestion of these DNAs with PST-1 (New England Biolabs), 3 of the 4 picked colonies were shown to possess plasmids containing inserts of 400–750 base pairs. Colony No. 3, the colony which retained the highest amount of hybridized labelled probe, had an insert containing an internal PST-1 site, giving rise to two fragments of approximately 600 and 150 base pairs upon PST-1 digestion.

The approximately 750 base pair (total) insert from Colony No. 3 was removed with PST-1 and subcloned (Maniatis et al., op. cit., p. 391) into PST-1 cut pUC 8 (Vieira et al., 1982, Gene 19: 259-268). One subclone, No. 44, contained the approximately 600 base pair insert. One liter of LB broth (with 100 μg ampicillin/ml) inoculated with bacteria containing the subclone No. 44 plasmid grown overnight at 37° C. and processed to prepare CsCl purified plasmid DNA (Garger, et al., 1983, Biochem. Biophys. Res. Comm. 117 No. 3, pp. 835–842).

EXAMPLE 12

Sequence Analysis of Subclone β44

20 μg of subclone No. 44 was digested with BamH-1 (New England Biolabs), then it was treated with calf alkaline phosphatase (Boehringer Mannheim) labeled at the 5' end with 0.33 mCi of [γ-$^{32}$P]-ATP (Amersham, 3000 and T4 polynucleotide kinase (New England Biolabs) by the method of Maxim et al., Methods in Enzymology, 1977, 65: 499–560. The labelled DNA was digested with HindII. (New England Biolabs) and the 600 base pair insert was purified by electroelution (Maniatis et al., op. cit., p. 164) and NACS-PREPAC A change in the underlined codon ATT to ATG yields a different peptide having methionine at that position instead of isoleucine. The C-terminal fragment of this peptide, Leu Ala Gly Pro Arg Ser Leu Arg Arg Ser Ser Cys Phe Gly Gly Arg Met Asp Arg Ile Gly Ala Gln Ser Gly Leu Gly Cys Asn Ser Phe Arg Tyr Arg Arg, corresponds to the C-terminal amino acid sequence of the human ANF peptide. This peptide can also be synthesized chemically using known peptide synthesis techniques.

What is claimed is:

1. A peptide or the amide thereof having the amino acid sequence: X-Cys Phe Gly Gly Arg Met Asp Arg Ile Gly Ala Gln Ser Gly Leu Gly Cys Ans Ser-Y wherein X is the N-terminal amino group of cysteine, or Ser
Ser Ser
Arg Ser Ser
Arg Arg Ser Ser
Leu Arg Arg Ser Ser
Arg Ser Leu Arg Arg Ser Ser
Pro Arg Ser Leu Arg Arg Ser Ser
Gly Pro Arg Ser Leu Arg Arg Ser Ser
Ala Gly Pro Arg Ser Leu Arg Arg Ser Ser
Leu Ala Gly Pro Arg Ser Leu Arg Arg Ser Ser and wherein Y is the carboxyl group of serine or
Phe
Phe Arg
Phe Arg Try
Phe Arg Try Arg, or
Phe Arg Tyr Arg Arg.

2. A peptide according to claim 1 having the amino acid sequence:
Met Asp Phe Lys Asn Leu Leu Asp His Leu Glu Glu Lys Met Pro Val Glu Asp Glu Val Met Pro Pro Gln Ala Leu Set Glu Gln Thr Asp Glu Ala Gly Ala Ala Leu Ser Ser Leu Ser Glu Val Pro Pro Trp Thr Gly Glu Val Asn Pro Ser Gln Arg Asp Gly Gly Ala Leu Gly Arg Gly Pro Trp Asp Pro Ser Asp Arg Ser Ala Leu Leu Lys Ser Lys Leu Arg Ala Leu Leu Ala Gly Pro Arg Ser Leu Arg Arg Ser Ser Cys Phe Gly Gly Arg Met Asp Arg Ile Gly Ala Gln Ser Gly Leu Gly Cys Asn Ser Phe Arg Tyr Arg Arg.

3. A composition for treating a disorder of electrolyte balance or altered vascular resistance comprising a therapeutically active amount of a peptide of claim 1 in a suitable carrier.

4. A peptide or the amide thereof having the amino acid sequence:

Leu Ala Gly Pro Arg Ser Leu Arg Arg Ser Ser Cys Phe Gly

Gly Arg Met Asp Arg Ile Gly Ala Gln Ser Gly Leu Gly Cys

Asn Ser Phe Arg Tyr Arg Arg.

5. A peptide having the amino acid sequence

Arg Arg Ser Ser Cys Phe Gly Gly Arg Met Asp Arg Ile Gly

Ala Gln Ser Gly Leu Gly Cys Asn Ser Phe Arg Tyr.

6. A peptide or the amide thereof having the amino acid sequence:

Arg-Ser-Ser-Cys-Phe-Gly-Gly-Arg-Met Asp-Arg-Ile-Gly-Ala Gln-Ser-Gly-Leu-Gly-Cys-Asn-Ser-Phe-Arg-Tyr.

* * * * *